US012692537B2

(12) United States Patent
Liu et al.

(10) Patent No.: US 12,692,537 B2
(45) Date of Patent: Jul. 28, 2026

(54) LABELING OF OLIGONUCLEOTIDE PROBES BY MULTIPLE-WAY LIGATION

(71) Applicant: Deutsches Krebsforschungszentrum Stiftung des öffentlichen Rechts, Heidelberg (DE)

(72) Inventors: Hai-Kun Liu, Weinheim (DE); Yong-Sheng Cheng, Schriesheim (DE)

(73) Assignee: DEUTSCHES KREBSFORSCHUNGSZENTRUM STIFTUNG DES OFFENTLICHEN RECHTS, Heidelberg (DE)

( * ) Notice: Subject to any disclaimer, the term of this patent is extended or adjusted under 35 U.S.C. 154(b) by 495 days.

(21) Appl. No.: 16/494,639

(22) PCT Filed: Mar. 6, 2018

(86) PCT No.: PCT/EP2018/055422
§ 371 (c)(1),
(2) Date: Sep. 16, 2019

(87) PCT Pub. No.: WO2018/188856
PCT Pub. Date: Oct. 18, 2018

(65) Prior Publication Data
US 2020/0087719 A1      Mar. 19, 2020

(30) Foreign Application Priority Data
Apr. 13, 2017    (EP) ..................................... 17166584

(51) Int. Cl.
*C12Q 1/6841* (2018.01)
*C12Q 1/682* (2018.01)

(52) U.S. Cl.
CPC ........... *C12Q 1/6841* (2013.01); *C12Q 1/682* (2013.01); *C12Q 2525/191* (2013.01); *C12Q 2533/107* (2013.01); *C12Q 2565/1025* (2013.01)

(58) Field of Classification Search
None
See application file for complete search history.

(56) References Cited

U.S. PATENT DOCUMENTS

| | | | | | |
|---|---|---|---|---|---|
| 6,001,614 A | * | 12/1999 | Akhavan-Tafti | ....... | C12N 15/10 435/6.1 |
| 2005/0019776 A1 | * | 1/2005 | Callow | ................ | C12Q 1/6855 435/6.1 |
| 2006/0003333 A1 | * | 1/2006 | Puskas | ................. | C12Q 1/6818 435/6.11 |
| 2015/0051105 A1 | * | 2/2015 | Ueno | ................... | C12Q 1/6837 506/9 |

FOREIGN PATENT DOCUMENTS

| | | |
|---|---|---|
| EP | 3299472 | 3/2018 |
| JP | 2013-90622 A | 5/2013 |
| WO | 00/05412 A1 | 2/2000 |
| WO | 2012/148477 | 11/2012 |

OTHER PUBLICATIONS

Willis (Prenatal Diagnosis 2012, 32, 315-320).*
Raj et al., "Imaging individual mRNA molecules using multiple singly labeled probes", Nature Methods, vol. 5, No. 10, pp. 877-879, Sep. 21, 2008.
International Search Report and Written Opinion, International Patent Application No. PCT/EP2018/055422, May 23, 2018 (15 pages).

* cited by examiner

*Primary Examiner* — Anne M. Gussow
(74) *Attorney, Agent, or Firm* — Merchant & Gould P.C.

(57) ABSTRACT

The present invention provides a novel method for multiple labelling of nucleic acid probes by ligation. The method uses a ligase catalysed reaction to connect a nucleic acid probe with multiple pre-prepared nucleic acid label carrier molecules under the presence of a stabilizing complementary adaptor oligonucleotide. The method allows for an easy, cheap and fast labelling of multiple probes with multiple different labels. In this way, the costs and effort for the generation of single molecule Fluorescent In Situ Hybridization (smFISH) assays was significantly reduced, allowing combinatorial multi-color barcoding of nucleic acid probes The invention further provides methods for the generation of FISH libraries and labelling kits comprising the novel tools of the invention.

13 Claims, 4 Drawing Sheets

LABELING OF OLIGONUCLEOTIDE PROBES BY MULTIPLE-WAY LIGATION

FIELD OF THE INVENTION

Figure 1A:
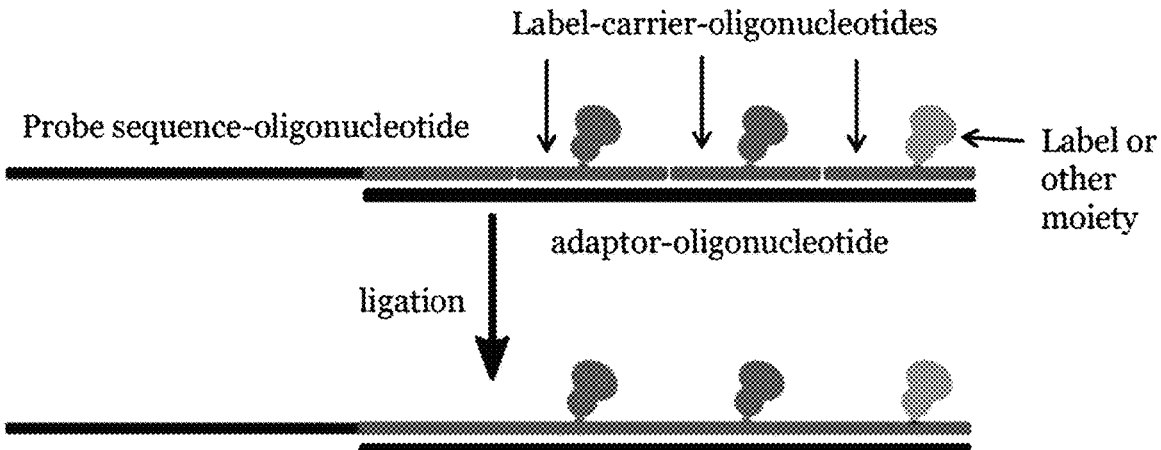
Figure 1B:
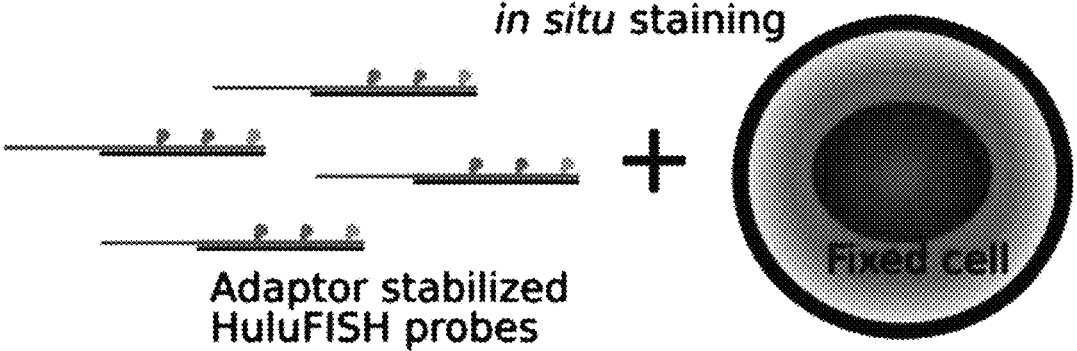

The present invention provides a novel method for multiple labelling of nucleic acid probes by ligation. The method uses a ligase catalysed reaction to connect a nucleic acid probe with multiple pre-prepared nucleic acid label carrier molecules under the presence of a stabilizing complementary adaptor oligonucleotide. The method allows for an easy, cheap and fast labelling of multiple probes with multiple different labels. In this way, the costs and effort for the generation of single molecule Fluorescent In Situ Hybridization (smFISH) assays was significantly reduced, allowing combinatorial multi-color barcoding of nucleic acid probes. The invention further provides methods for the generation of FISH libraries and labelling kits comprising the novel tools of the invention.

DESCRIPTION

Since the invention of in situ hybridization (ISH) by Joseph G. Gall and Mary-Lou Pardue more than 40 years ago, this powerful technique has tremendously transformed basic research (i.e. gene expression, etc.) and diagnostics for biomarker detection. Only through ISH, researchers were able to study gene expression and diagnose biomarker level with spatio-information. Nowadays, ISH and its derivatives have become the working horse in a variety of fields, including histology, single cell biology, etc. There were even omics-scale efforts trying to have a complete gene expression atlas like Allen Brain Atlas based on ISH. With the advances in fluorophore chemistry and microscopy hardware, Fluorescence in situ hybridization (FISH) has gained more attentions due to its superior low background and nm-scale spatio-localized signal (vs diffusive signal generated in enzymatic reaction from ISH), and could serve as good alternative for ISH, especially in future applications in the precision medicine where requiring digital and spatiotemporal quantification of biomarkers.

Since 90s, FISH has been innovatively used by Robert Singer and colleagues to image individual mRNA transcripts in situ at single molecular level (smFISH) from then gene expression or biomarker detection could be done in a digital and single molecular fashion (FIG. 1). However the first probe library was made from five gene-specific different custom-synthesized penta-fluorophore labelled oligos, which is still very expensive nowadays and make this powerful invention to be not applicable for every gene. From 2008, Arjun and colleagues invented a pooled single fluorophore labelling method based on classical NHS (N-Hydroxysuccinimide) conjugation chemistry, which greatly downsizes the cost of probe library. And this novel labelling is now licensed by Biosearch Technologies Inc. So research and clinical users could use this technique at price of ~760 euro for 100-400 reactions. This exceptionally high cost for using the commercial FISH probe library is a fundamental limitation of smFISH, as well as its low throughput, typically smFISH approach allow probing only a few genes at a time. This low throughput is due to a lack of distinguishable probes with which to label cells and the cost of producing large amounts of labeled probe required for high efficient staining. Thus, improvements in smFISH probe generation and improving detection efficiency is necessary.

EP application No. 16190862.9 discloses a ligation based method for generating labelled oligonucleotides. However, the method ligates a probe sequence with a multiple labelled second oligo. Multiple labelling of one oligo may however lead to spacing problems due to interference such as quenching between the label moieties.

Before the present invention is described, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The above problem is solved by a method for producing a labelled or otherwise modified, oligonucleotide probe, the method comprising the steps of:

(a) Providing a probe-sequence-oligonucleotide comprising (i) a probe sequence comprising a nucleotide sequence complementary to a target nucleic acid and (ii) a predetermined tag nucleotide sequence complementary to a first adaptor nucleotide sequence, (b) Providing a label-carrier-oligonucleotide comprising at least one labeling moiety, or other functional moiety, wherein the label-carrier-oligonucleotide has a predetermined tag nucleotide sequence complementary to a second adaptor nucleotide sequence, (c) Providing an adaptor-oligonucleotide, comprising in direct sequence the first and the second adaptor nucleotide sequence;

(d) Bringing into contact under hybridizing conditions the probe-sequence-oligonucleotide, the label-carrier-oligonucleotide and the adaptor-oligonucleotide, to form a complex, wherein, in the complex, a free (unblocked) -OH group is in close spatial proximity to a free (unblocked) phosphate group, (e) Reacting the complex to form a covalent bond between the 3'-OH group and the 5'-phosphate group using a ligase under ligating conditions, to form the labeled, or otherwise modified, oligonucleotide probe, (f) Optionally, removing the adaptor-oligonucleotide.

The inventive method may be used both for the attachment of label-carrier-oligonucleotides to the 3' and to the 5' end of the probe-sequence-oligonucleotide. Therefore, a method of the invention in one embodiment is preferable wherein in the probe-sequence-oligonucleotide the probe sequence is 5' of the predetermined tag nucleotide sequence, and in the adaptor-oligonucleotide, the first and second adaptor nucleotide sequence are in 3' to 5' direction in direct sequence, and in the complex in step (d) the free 3' OH group of the probe-sequence-oligonucleotide is in close spatial proximity to the free (unblocked) phosphate group of the label-carrier-oligonucleotide. In an alternative embodiment of the invention, there is provided a method wherein in the probe-sequence-oligonucleotide the probe sequence is 3' of the predetermined tag nucleotide sequence, and in the adaptor-oligonucleotide, the first and second adaptor nucleotide sequence are in 5' to 3' direction in direct sequence, and in the complex in step (d) the free (unblocked) phosphate group of the probe-sequence-oligonucleotide is in close spatial proximity to the free 3' OH group of the label-carrier-oligonucleotide.

The methods and compounds of the invention allow for a quick, cheap and easy labelling of nucleic acid probes. The idea of the invention is to provide a system that allows the practitioner to label any given oligonucleotide probe (probe-sequence-oligonucleotide) on the shelf without the need to attach the label-moiety to the individual probe sequence—which is expensive and therefore impairs the generation of libraries of many labelled individual probes. To this end, the invention now provides a system comprising one or preferably more pre-prepared label-carrier-oligonucleotide, wherein each label-carrier-oligonucleotide comprises a different label, or other modification. The invention then provides an adaptor oligonucleotide with a sequence complementary to the predetermined tag nucleotide sequence(s) in the probe-sequence oligonucleotide and in the label-carrier-oligonucleotides to assemble these molecules into a complex where they can be fused together by simple ligation. In this way the invention provides an easy approach to attach multiple different labels to a nucleotide sequence probes by ligation. Using only a few, preferably only one label or other modification for each of the ligated label-carrier-oligonucleotides, each of these labels are also sufficiently spaced from each other to avoid interference.

Most preferably the method of the invention in step (b) comprises providing a first, and a second, optionally a third or more (a fourth, fifth, sixth, . . . $50^{th}$ . . . $100^{th}$, etc.), label-carrier-oligonucleotides, wherein the first label-carrier-oligonucleotide has a predetermined tag nucleotide sequence complementary to a second adaptor nucleotide sequence, the second label-carrier-oligonucleotide has a predetermined tag nucleotide sequence complementary to a third adaptor nucleotide sequence, optionally, the third or more label-carrier-oligonucleotide has a predetermined tag nucleotide sequence complementary to a fourth or more adaptor nucleotide sequence, and wherein in step (c) the adaptor-oligonucleotide comprises in direct sequence the first, the second, the third, optionally thee fourth or more, adaptor nucleotide sequence. In this embodiment the probe-sequence-oligonucleotide of the invention can be labelled easily with multiple labels or other moieties.

In context of the invention, when referring to a specific oligonucleotide, or probe, or to other expressions describing nucleic acids, the person of skill will recognize that the expression refers not to single molecules, but to a single species of molecules. In practical application in the laboratory, the person of skill uses preparations of a multitude of molecules of a species of, for example, one oligonucleotide sequence. In such a population of molecules usually all nucleotides are identical, except where the oligonucleotides were produced to contain a random sequence region, for example during oligonucleotide synthesis. This can be achieved by polymerising the oligonucleotide with an equal mixture of more than one type of nucleotide, which then are coupled by chance. In this event the species of oligonucleotides in the mixture contains a "degenerated" sequence.

The term "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, peptide nucleic acid (PNA), locked nucleic acid (LNA), or the like.

The term "nucleic acid" refers to a polymer of any length, e.g., greater than about 2 bases, greater than about 10 bases, greater than about 100 bases, greater than about 500 bases, greater than 1000 bases, up to about 10,000 or more (e.g., 100,000,000 or more) bases composed of nucleotides, e.g., deoxyribonucleotides or ribonucleotides, and may be produced enzymatically or synthetically which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine/uracil (G, C, A and T/U, respectively).

The term "oligonucleotide" as used herein denotes a single stranded multimer of nucleotide of from about 2 to about 500 nucleotides. Oligonucleotides may be synthetic or may be made enzymatically. Oligonucleotides may contain ribonucleotide monomers (i.e., may be oligoribonucleotides), deoxyribonucleotide monomers or a combination of the two. Oligonucleotides may be 10 to 20, 11 to 30, 31 to 40, 41 to 50, 51-60, 61 to 70, 71 to 80, 80 to 100, 100 to 150, 150 to 200 or 200-250 or up to 500 nucleotides in length.

The term "hybridization" refers to the specific binding of a nucleic acid to a complementary nucleic acid via Watson-Crick base pairing. Accordingly, the term "in situ hybridization" refers to specific binding of a nucleic acid to a complementary nucleic acid inside a cell or in an intact chromosome. The terms "hybridizing" and "binding", with respect to nucleic acids, are used interchangeably.

The term "hybridizing conditions" is intended to mean those conditions of time, temperature, and pH, and the necessary amounts and concentrations of reactants and reagents, sufficient to allow at least a portion of complementary sequences to anneal with each other. As is well known in the art, the time, temperature, and pH conditions required to accomplish hybridization depend on the size of the oligonucleotide molecules to be hybridized, the degree of complementarity between the oligonucleotides to be hybridized, and the presence of other materials in the hybridization reaction admixture, salts etc. The actual conditions necessary for each hybridization step are well known in the art or can be determined without undue experimentation.

The term "in situ hybridization conditions" as used herein refers to conditions that allow hybridization of a nucleic acid to a complementary nucleic acid, e.g., a sequence of nucleotides in a RNA or DNA molecule and a complementary oligonucleotide, in a cell. Suitable in situ hybridization conditions may include both hybridization conditions and optional wash conditions, which conditions include temperature, concentration of denaturing reagents, salts, incubation time, etc. Such conditions are known in the art.

In some embodiments of the invention, the probe-sequence-oligonucleotide, the label-carrier-oligonucleotide and the adaptor-oligonucleotide are single stranded nucleic acid molecules, preferably RNA and/or DNA. Furthermore, all nucleic acid molecules may contain unnatural or modified nucleic acid residues, such as O-methly modified residues. However, specifically preferred are DNA oligonucleotides which are easier and cheaper to synthesize.

It is in some embodiments preferred that the probe-sequence-oligonucleotide does not comprise a modification of the 3' terminal OH group and/or 5' terminal phosphate group of the polynucleotide, in particular it is preferable that the probe-sequence-oligonucleotide does not comprise a terminal amine group. In context of the invention it is likely that the probe-sequence-oligonucleotide will be chemically synthesized according to state of the art oligonucleotide synthesis procedures. Such procedures often include the use of masking or blocking groups, which preferably are all removed before applying the probe-sequence-oligonucleotide to the method of the invention. Also, synthesis of oligonucleotides often results in a 5 prime terminal OH group. In some embodiments where the label-carrier-oligonucleotide is ligated to the 5 prime end of the probe-sequence-oligonucleotide, it is necessary to attach a terminal 5 prime phosphate group to allow for the ligation reaction.

In some embodiments it is preferable that the label-carrier-oligonucleotide comprises preferably at least one, in other embodiments two or more, preferably three, four or five, labelling moieties, or other functional moieties. However, in more preferred embodiments the label-carrier-oligonucleotide comprises only one, or not more than two or three, of such labelling moieties, or other functional moieties. According to the invention each probe-sequence-oligonucleotide can be labelled with multiple labels by using a plurality of label-carrier-oligonucleotide which are all ligated to the probe-sequence-oligonucleotide in tandem by the method of the invention. Each of the label-carrier-oligonucleotide in the plurality of label-carrier-oligonucleotides then is labelled with a different label or modification. This embodiment allows a simultaneous probing of multiple target sequences such as mRNA species in a cell.

The label-carrier-oligonucleotide may be of any length suitable for ligation with the probe sequence oligonucleotide. Some preferred label-carrier-oligonucleotide of the invention are 5 to 200 nucleotides in length, preferably 5 to 100 nucleotides, more preferably 5 to 30, or 8 to 20, more preferably about 15. The sequence of the label-carrier-oligonucleotide in preferred embodiments should allow for a specific binding of the predetermined tag nucleotide sequence to the respective adaptor sequence.

The label-carrier-oligonucleotide in one preferred embodiment comprises a 5 prime (free) phosphate group to allow for an enzyme catalysed ligation with the probe-sequence-oligonucleotide. In another embodiment the label-carrier-oligonucleotide comprises a 3 prime end terminal OH group (in case the labelling of the probe sequence oligonucleotide is performed on the 5' end.

The term "adaptor-oligonucleotide" generally refers to an oligonucleotide that comprises in a tandem arrangement at least two, preferably more, adaptor sequences which are complementary to the predetermined tag nucleotide sequences in the probe-sequence-oligonucleotide and the label-carrier-oligonucleotide(s). The adaptor sequences are therefore also predetermined. It is in some embodiments that the sequences of the predetermined tag nucleotide sequences and by complementarity also the corresponding adaptor sequences, in the probe-sequence oligonucleotide and each of the label-carrier-oligonucleotides are different from each other. In an embodiment where the labelling of the probe-sequence-oligonucleotide is performed on its 3' end, the adaptor-oligonucleotide comprises in consecutive order from its 3' to 5' end the first, then the second adaptor-sequence. If additional label-carrier-oligonucleotides are used, the adaptor-sequences are added consecutively to the 3' end of the adaptor-oligonucleotide (third, fourth, fifth etc.). The order will be in 5' to 3' if the labelling is performed on the 5' end of the probe-sequence-olignucleotide. In this way, when brought into contact under hybridizing conditions, the probe-sequence-oligonucleotide, all label-carrier-oligonucleotides and the adaptor-oligonucleotide form a double stranded complex in which the strand composed of the probe-sequence-oligonucleotide and all label-carrier-oligonucleotides comprises ligatable "nicks" between each individual oligonucleotide. A ligatable nick is a gap between two oligonucleotides narrow enough to allow a 3'OH and 5'phosphate group to engage in an enzyme catalysed ligase reaction to form a covalent bond and thereby phosphodiester backbone. In some embodiments the 3' and 5' ends of the adaptor-oligonucleotide can be modified so that they cannot engage in a ligation reaction to avoid any unwanted by-products during ligation.

The adaptor-oligonucleotide comprises preferably two or more adaptor sequences each having at least 3, preferably 4, 5, 6, 7, 8, or more nucleic acid positions, preferably 8 to 20, 10 to 20, 12 to 18 more preferably about 15. In some embodiments each adaptor sequence consists of a sequence reverse complementary (when seen 5' to 3') to the respective predetermined tag nucleotide sequence. The degree of complementarity between the adaptor sequence of the adaptor-oligonucleotide and the corresponding predetermined tag nucleotide sequence of label-carrier-oligonucleotide or probe-sequence-oligonucleotide is selected to allow for the stable hybridization of the two sequences under conditions suitable for performing a ligation. In this context the degree of reverse complementarity is preferably at least 90%, most preferably 95% or 100%.

In preferred embodiments, in addition to the afore described, the adaptor-oligonucleotide does not comprise a degenerate overhang at either the 3' and/or 5' end, preferably not at the end that when the complex is formed is capable of hybridizing with the probe sequence in the probe-sequence-oligonucleotide.

In some embodiments the method of the invention may further comprise a step of purifying the ligated product of the probe-sequence-oligonucleotide and label-carrier-oligonucleotide(s). The ligation product forms the labelled, or otherwise modified, oligonucleotide probe, and, therefore, the product of the inventive process. Purification may be done by any means known to the skilled artisan for purifying nucleic acid probes, and includes but is not limited to, purification via gel electrophoreses, such as PAGE. Most preferably the single stranded ligated product is first purified and subsequently in a second step again hybridized with the adaptor-oligonucleotide to stabilize the probe prior use.

The term "ligase" as used herein refers to an enzyme that is commonly used to join polynucleotides together or to join the ends of a single polynucleotide. A ligase of the invention is preferably selected from ATP-dependent double-strand polynucleotide ligases, NAD+-dependent double-strand DNA or RNA ligases, and single-strand polynucleotide ligases, and are preferably selected from bacterial ligases, such as *E. coli* DNA ligase, Taq DNA ligase, Ampligase® thermostable DNA ligase, phage ligases, such as $T_3$ DNA ligase, $T_4$ DNA ligase, $T_7$ DNA ligase and mutants thereof, including fusion ligases containing a DNA-binding domain and a ligase, such as $Sso_7$-$T_3$ DNA ligase, $Sso_7$-$T_4$ DNA ligase, $Sso_7$-$T_7$ DNA ligase, $Sso_7$-Taq DNA ligase, $Sso_7$-*E. coli* DNA ligase, $Sso_7$-Ampligase, DNA ligase $Sso_7$, $T_4$ RNA ligase 1, $T_4$ RNA ligase 2, and $T_4$ truncated and mutated (K227Q) RNA ligase. Most preferably is the use of $T_4$ DNA ligase, because this enzyme is robust, cheap and efficient.

The term "target" refers to a biological entity that can be spatially separated, hybridized to a probe, and visualized. Cells, individual chromosomes, and material deposited in an array are examples of targets. In context of the invention the target nucleic acid is a target single stranded nucleic acid, that comprises a sequence having at least one, preferably multiple, binding regions for nucleic acid probes as produced by the method of the present invention. In preferred embodiments the target nucleic acid is a messenger RNA (mRNA).

A label in context of the invention is a detectable moiety that may produce a signal directly or indirectly. One example of a detectable moiety that produces a signal directly is a fluorescent molecule. Detectable moieties that produce a signal indirectly include moieties that produce a signal upon exposure to detection reagents such as substrates or antibodies, etc. A detectable moiety that produces a signal directly can optionally be detected by indirect means such as by using a labeled antibody that binds to the moiety. In certain cases, a signal may be of a particular wavelength that is detectable by a photodetector, e.g., a light microscope, a spectrophotometer, a fluorescent microscope, a fluorescent sample reader, or a florescence activated cell sorter, etc. A labeling moiety in context of the invention may be any moiety that allows for detection of the presence or absence of the moiety. Suitable labels include fluorescent dyes that include xanthene dyes, e.g. fluorescein and rhodamine dyes, such as fluorescein isothiocyanate (FITC), 6-carboxyfluorescein (commonly known by the abbreviations FAM and F),6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g. umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy$_3$, Cy$_5$, etc; BODIPY dyes and quinoline dyes. Specific fluorophores of interest that are commonly used in some applications include: pyrene, coumarin, diethylamino-coumarin, FAM, fluorescein chlorotriazinyl, R110, eosin, JOE, R6G, tetramethylrhodamine, TAMRA, lissamine, ROX, napthofluorescein, Texas red, napthofluorescein, Cy$_3$, and Cy$_5$, etc. Suitable distinguishable fluorescent label pairs useful in the subject methods include Cy-$_3$ and Cy-$_5$ (Amersham Inc., Piscataway, N.J.), Quasar 570 and Quasar 670 (Biosearch Technology, Novato Calif.), preferably the following four Alexa dyes: Alexa fluor 488, Alexa fluor 555, Alexa fluor 594 and Alexa fluor 647 (Molecular Probes, Eugene, Oreg.); Atto dyes: Atto488, Atto565, Atto594, Atto647N, Atto750 (Atto-Tec GmbH); BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002).

The phrase "distinguishable labels" or "different-color labels" or any grammatical equivalent thereof refers to labels can be independently detected and measured, even when the labels are mixed. In other words, the amounts of label present (e.g., the amount of fluorescence) for each of the labels are separately determinable, even when the labels are co-located (e.g., in the same tube or in the same duplex molecule or in the same cell). The above labels may be used as distinguishable labels. Some preferred distinguishable fluorescent label pairs include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 and TOPRO3 (Molecular Probes, Eugene, Oreg.), and preferably FAM and ATTO550. Further suitable distinguishable detectable labels may be found in Kricka et al. (Ann Clin Biochem. 39:114-29, 2002).

The term "predetermined" refers to something that is known before use.

Preferably the probe-sequence-oligonucleotide to be used in the methods of the invention has a length of between 20 to 300 nucleotides. Depending on which kind of target nucleic acid is to be detected by the probe produced according to the invention, the length of the probe is selected. Although for the application of smFISH probes the length of the probes is selected to be below 500 bases, other applications may require the use of longer nucleic acid probes. Since the length of the probe sequence is not important for the labelling process, the present invention shall not be limited to any specific lengths. Preferred is however a probe sequence for use in smFISH. In the probe sequence oligonucleotide the predetermined tag nucleotide sequence has a length of at least 5 nucleic acids, preferably 6, 7, 8, 9, 10 or 15 or more, more preferably 5 to 50, 5 to 20, more preferably 10 to 20, 12 to 18, most preferably about 15 nucleic acids.

The problem is furthermore solved by a method for generating a single molecule Fluorescent In Situ Hybridization (smFISH) probe library, comprising producing at least two fluorescent labeled oligonucleotide probes according to a labelling method of the above disclosed invention, wherein the at least two fluorescent oligonucleotide probes are capable of binding to one target nucleic acid.

Some embodiments of the invention pertain to the above library generation method where the at least two fluorescent labeled oligonucleotide probes are capable of binding the one target nucleic acid at different, preferably non-overlapping, locations (sequences). The at least two fluorescent labeled oligonucleotide probes in a library of the invention are at least 10, preferably at least 30, more preferably 30 to 150, and most preferably about 100 fluorescent labeled oligonucleotide probes, and wherein each of said fluorescent labeled oligonucleotide probes is capable of binding to the one target nucleic acid, preferably at non-overlapping positions.

In some preferred embodiments of this aspect, at least two of the at least two fluorescent labeled oligonucleotide probes in the library are labeled with multiple label moieties, however, preferably wherein each labeled oligonucleotide probe in the library comprises an identical label, or identical label combination. A library of nucleic acid probes in context of the invention shall denote a set of probes for probing and detecting one nucleic acid molecule, for example one mRNA in a smFISH approach.

In another aspect of the invention there is provided a method for probing a target sequence of messenger ribonucleic acid molecules (mRNA's) in cell, said target sequence including multiple non-overlapping probe binding regions, comprising immersing said cell in an excess of at least two oligonucleotide probes, wherein each oligonucleotide probe is multiple labeled with the same combination of at least two different-color fluorescent labels, and each containing a nucleic acid sequence that is complementary to a different probe binding region of said target sequence; washing said fixed cell to remove unbound probes; and detecting fluorescence from said probes.

Different-color fluorescent labels in context of the invention are fluorescent moieties having different excitation and/or signal wave-lengths, and therefore allow for an individual detection.

Another aspect of the invention further relates to a method for probing at least two target sequences of messenger ribonucleic acid molecules (mRNA's) simultaneously in a cell, said target sequences each including multiple non-overlapping probe binding regions, comprising immersing said cell in an excess of probe sets, one probe set for each target sequence, wherein each probe set comprises at least two oligonucleotide probes, and each oligonucleotide probe of a probe set is multiple labeled with an identical combination of at least two different-color fluorescent labels, to provide a color bar code for each target sequence, and wherein the combination of different-color fluorescent labels is different between each probe set, and wherein each oligonucleotide probe in a probe set contains a nucleic acid sequence that is complementary to a different probe binding region of said target sequence; washing said fixed cell to remove unbound probes; and detecting fluorescence from said probes.

In context of the invention the cell is preferably a fixed and permeabilized cell.

In this aspect the "oligonucleotide probe(s)" are prepared preferably according to a labeling method of the invention as disclosed herein above.

The number of probe binding regions in the target mRNAs and probes may in some embodiments be 40 to 60. In other embodiments the at least 30 probes have target-complementary sequences that are 7-40 nucleotides in length, most preferably that are 15-30 nucleotides in length.

Each probe may be added to the cell in a concentration of 0.2-10 nanograms per microliter.

The fixed cells are preferably prepared by formaldehyde fixation.

Detection includes preferably imaging with a wide-field fluorescence microscope.

Furthermore provided is a labelling kit for labelling an oligonucleotide probe, the kit comprising a first, and a second, optionally a third or more, label-carrier-oligonucle-otides, wherein the first label-carrier-oligonucleotide has a predetermined tag nucleotide sequence complementary to a second adaptor nucleotide sequence, the second label-car-rier-oligonucleotide has a predetermined tag nucleotide sequence complementary to a third adaptor nucleotide sequence, optionally, the third or more label-carrier-oligo-nucleotide has a predetermined tag nucleotide sequence complementary to a fourth or more adaptor nucleotide sequence; and an adaptor-oligonucleotide comprising in direct sequence a first, the second, the third, optionally thee fourth or more, adaptor nucleotide sequence, wherein the first adaptor nucleotide sequence is complementary to a predetermined tag nucleotide sequence in a probe-sequence-oligonucleotide (or oligonucleotide probe).

The labeling kit of the invention may further comprise a ligase, optionally together with buffers or reagents for its use. Preferable ligases are described herein above.

The labeling kit of the invention may further comprise instructions for its use.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Multiple fluorophore labelling based on the invention. (a) Multiple-way ligation based fluorophore labelling. (b) in situ staining with probes prepared with the invention and pre-annealed with the adaptor-oligonucleotide for avoiding multiple color fluorescence quenching. (c) Gapdh expression in Hepa 1-6 with the Gapdh FISH probe conjugated with Atto488, Atto565, and Atto647N, without adaptor-oligonucleotide stabilization. (d) Gapdh mRNA visualized as individual dots by adaptor-oligonucleotide pre-annealed probe in (c).

FIG. 2: FISH 3-color combinatorial barcoding for in vivo detection of developmental genes in mouse embryonic brain. (a) Color coding scheme for FISH from 3 base colors. (b) 7-gene detection in E12.5 mouse embryonic brain ventricular zone—Scale bar 5 μm. (c) mRNA transcripts quantification for these 7 developmental genes.

EXAMPLES

In the previous patent application EP 16190862.9 (incorporated herein by reference), a T4 DNA ligase (T4DL) has been used to efficiently and cost-effectively produce fluorescent labelled probes for smFISH. However, due the chemistry of the fluorescent pre-labelled oligos, there are increasing difficulties and costs associated to produce multiple fluorophore labelled oligos by state-of-art oligo synthesis and labelling techniques. Aiming for cost-effectiveness and breaking down the technical challenge, an alternative version of the previous method has been developed. The rationale behind the method of the present invention is harnessing the multiple-way ligation capability of T4DL (T4 DNA Ligase) or other dsDNA ligases such as T7 DNA ligase. The unlabelled smFISH oligo pool is synthesized with a common predetermined tag nucleotide sequence and single/multiple fluorescent labelled oligos (label-carrier-oligonucleotides) and an adaptor-oligonucleotide. After a one-pot ligation reaction, the smFISH probe will be conjugated to 3-fluorescent oligos from the 5 to the 3 end, as shown in FIG. 1A. The spacing between the individual labels is about 15 nucleotides.

Figure 1C:
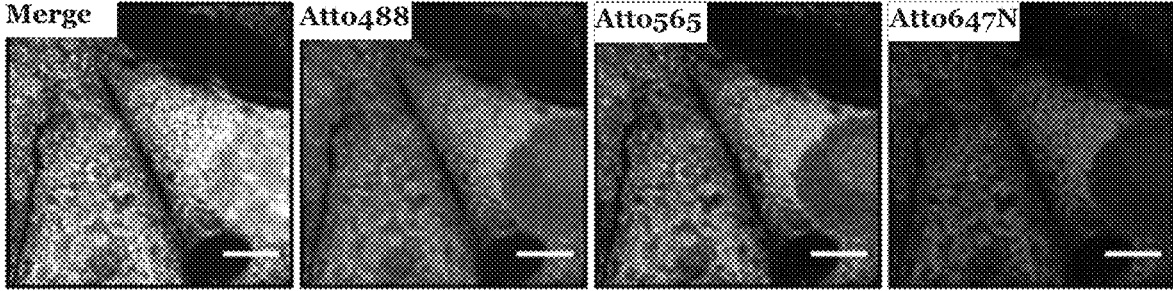
Figure 1D:
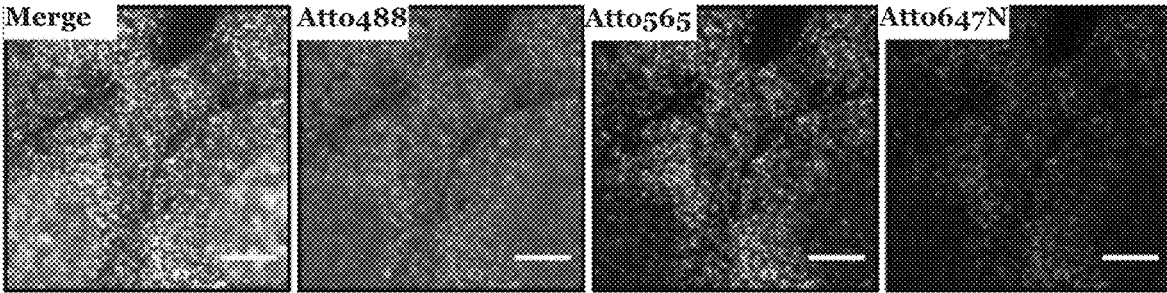

With the stabilization by the adaptor oligo, individual clear dots can be obtained in all 3 channels for Gapdh probes labeled with one copy of Atto488, Atto565, and Atto647N (FIGS. 1c and 1d). With the multiple labelling capacity of the method, the inventors could assign various color combinations to a panel of genes, and decode the dots by counting their appearance in channels. The evolved multiple fluorophore labelling capability with smFISH extends the conventional smFISH with an autonomous combinatorial color barcoding mechanism. Each color combination is covalently linked with the individual probe, therefore the fluorophore stoichiometry is invariable between probes. During image acquisition, the intensity ratio between fluorophores will be independent on the brightness of FISH dots. The barcoding capacity simply increases with the exponentials of the channel (fluorophore choice) number n (the theorectical number of combinations is the sum of all color combinations is 2n−1). If FISH dot imaging is accurate enough and the relative ratio between the maximal intensity in each channel can be determined, the combinations can be higher.

Figure 2A:
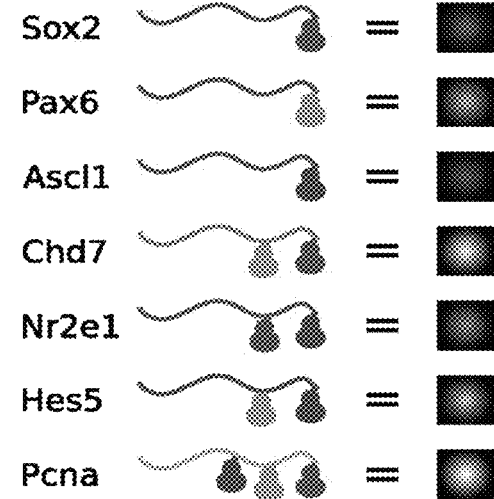
Figure 2B:
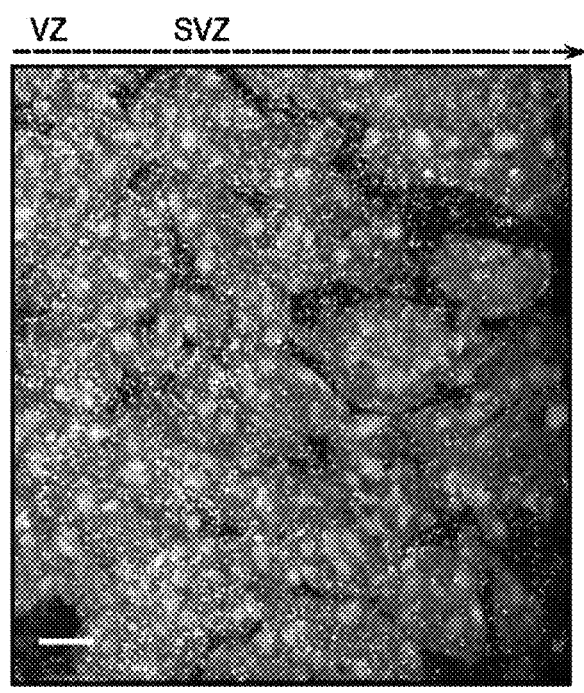
Figure 2C:
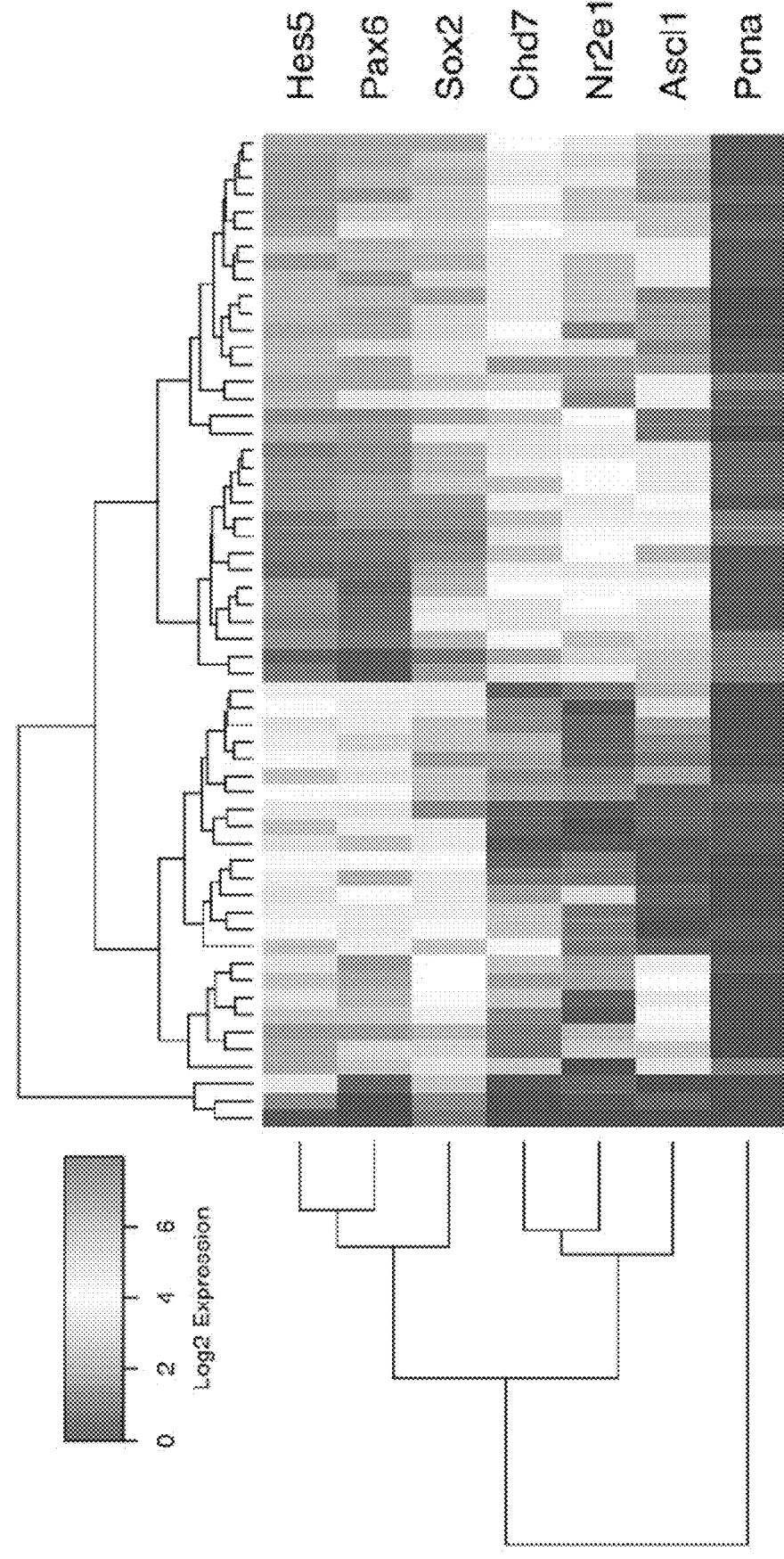

One of the most interesting applications for smFISH is exploring the multiple gene expression pattern in tissue samples. Just with 3 base colors, the color combinations can be used to detect 7 genes in one round of hybridization. Here the inventors used embryonic day 12.5 (E12.5) mouse embryo cryo-sections samples to visualize the tissue heterogeneity of 7 developmental related genes (FIG. 2a). Simultaneous $_7$-gene detection shows the cellular organization pattern of the developmental gene expression (FIG. 2b). Hierarchically clustering shows 4 clusters with various degree of expression of stem cell markers (FIG. 2c).

Methods

Cell Culture and Tissue Section Preparation

Mouse primary neural stem cell (NSC) was isolated from subventricular zone of 8 week adult male C57BL/6J mouse brain. Isolated tissue pieces were further chopped down into imm3 in size and digested with Accutase solution (Sigma, A6964) at 37° C. for 20 minutes. Cells were centrifuged down for 5 minutes at 250 g, then resuspended and cultured in serum free medium (DMEM/F-12 HEPES (ThermoFisher, 31330095) supplemented with 0.6% glucose, 20 mM HEPES (1M stock, Sigma, H0887), 0.2 mM Progesterone, 0.06 mM Putrescine, 2% B27, 20 ng/ml EGF, 10 ng/ml FGF, 0.1% ITSS, 1× penicillin/streptomycin, 0.36 U/ml Heparin (Sigma, H3149), 1.2% (w/v) NaHCO$_3$). For NSC culture on coated plate or coverslip, plate or coverslip were coated in phosphate-buffered saline (PBS) supplemented with mg/ml poly-1-lysine (Sigma, P7280), 0.0025 mg/ml laminin (Roche, 11243217001) at 37° C. overnight and then dried under the cell culture hood with UV radiation. Mouse Hepa 1-6 cells were cultured in DMEM medium with 10% fetal bovine serum and 1× penicillin/streptomycin. Hepa 1-6 cells were directly grown on coverslip without coating. Embryonic mouse brain tissue cryo-sections were cut at 6 to 10 μm from embryonic day 12.5 C57BL/6J mouse embryo embedded in Tissue-Tek O.C.T. (Sakura, 4583).

Coated NSC cells, adherent Hepa 1-6 cells or cryo-sections were fixed with 4% formaldehyde in PBS for 10 min and then quenched with 135 mM glycine in PBS for 10 min at room temperature. Fixed cells were then washed once with PBS and permeablized in 70% ethanol overnight at 4° C. All water used for FISH related buffers were diethyl pyrocarbonate (DEPC) treated. After permeabilization cells were stored in cryoprotectant (25% glycerol, 25% ethylene glycol, 0.1M phosphate buffer, pH 7.4) at −20° C. until FISH staining.

Probe Design smFISH probes based on the conventional design3 were implemented in a R script to select probes first with Primer3 to get all possible probes without too strong secondary structure from the input cDNA sequence using the standard condition for selecting right primer in Primer3. Then non-overlapping smFISH probes were selected with 2 bp gap. For HuluFISH probes, all probes from Primer3 were additionally calculated for their hybridization efficiency with DECIPHER package in R under the condition used for staining. And the probes were filtered to have hybridization efficiency above 0.9 (maximally 1) and then non-overlapping HuluFISH probes were selected as before. Adaptor sequences were randomly generated and controlled for strong secondary structure by UNAfold. Passed sequences were blasted against a local mouse and human transcripts database (ensemble release 87) for less or equal than 15 bp exact match.

HuluFISH Probe Labelling and Purification

The labelling method of the invention is denoted as "HuluFISH".

FISH probe oligo pools and adaptor oligos were synthesized from Sigma with lowest quality for purification (desalting). For individual gene, oligos were pooled together to have 100 μM total oligo concentration. Fluorescent oligos were purchased from Eurofins genomics with various dyes, including Atto dyes, Alexa dyes or Cy dyes. For probe labelling without additional tag sequence, ligation was performed in T4 DNA ligase buffer (NEB, B0202S), with 30 μM adaptor oligo with degenerative sequence, 3 μM unlabelled FISH probe oligo pool and fluorescent label oligo, 25% PEG8000, 30 U/μL T4 DNA ligase (NEB, M0202M). Ligation reaction was then incubated on a thermocycler, with 12 cycles of 37° C. 10 seconds/16° C. 5 minutes. For probe labelling with a tag sequence, ligation was performed as before with some modifications, such as 16.7 μM of all oligos components and the oligo pool, 50 U/μL T4 DNA ligase. Then the ligation mix was left in dark at room temperature for 2 hours. The ligation product was concentrated with 9 volumes of butanol and centrifuged as pellet at 20,000 g, 15 minutes at 4° C. colorful labelled oligo pellet was washed once with 100% ethanol and spin down to remove ethanol, then resolubilized in loading buffer (8M Urea, 1×TBE (Carl Roth, A118.1), 0.01% bromophenol blue and xylene cyanol). With 5 minute denaturing at 9° C, oligos were loaded onto 15% Urea-PAGE gel (8M Urea, 1×TBE, 15% Rotiphorese Gel 30 (Carl Roth, 3029.2), 0.05% ammonium per-sulfate, 0.05% tetramethylethylenediamine) pre-run at 300 V for 30 minutes. Running condition was usually 300 V, 30 minutes, or until the bromophenol blue reached the end. Gel bands with fluorescent dye-oligo conjugates were excised under the ambient light. Gel pieces were homogenised manually by microtube pestle (Sigma, Z359947-100EA), and then extracted with 500 μL 10 mM TE buffer (pH 8.5, 10 mM tris(hydroxymethyl)aminomethane (Tris), 1 mM Ethylenediaminetetraacetic acid (EDTA)) at room temperature overnight, protected from light by wrapping in aluminium foil. The extracted oligos in TE were concentrated again by butanol, and washed once by ethanol like before. The final pellets were dried in dark at room temperature for 5-10 minutes, and then resolubilized in H$_2$O. The concentration was determined by nanodrop one (ThermoFisher) as ssDNA.

FISH Probe Staining and Imaging

HuluFISH probe mix was adjusted to 10 nM for each single oligo in hybridization buffer (2×SSC (saline-sodium citrate), 10% dextran sulfate, 10% formamide, 1 mg/mL tRNA (Roche, 10109541001), 2 mM ribonucleoside vanadyl complex (NEB, S1402S), 0.2 mg/mL BSA). Gapdh-Quasar570 probe was purchased from Biosearch Technology, resuspended and performed the staining as instructed from the manufacturer. Hybridization was performed in a water bath at 30° overnight, with the sample faced down on the parafilm. Cells on coverslip or tissue sections on glass slide were washed with washing buffer (2×SSC, 10% formamide, 0.1% Tween-20) at 37° C. for 6×10 minutes. The last washing step included 0.5 μg/mL DAPI (4',6-diamidino-2-phenylindole) for nuclei staining. The sample was mounted in ProLong Gold Antifade (ThermoFisher, P10144), and cured for overnight. The sample then was either imaged on a widefield microscope (Zeiss Cell Observer) with 200 ms, 950 ms and 5000 ms for 405 nm, 488 nm and 561 nm channel, or on a confocal microscope with Airyscan (Zeiss LSM800, equipped with 405, 488, 561, and 647 nm laser) with maximal laser power in each channel. The sample was scanned with Airyscan technology with the optimal settings provided by Zeiss software.

Image Analysis

Except for the nuclear outline manually defined in ImageJ, all the image analysis was performed in R, and majorly based upon the package EBImage. All intensity threshold values were based on the arbitrary units generated from Zeiss Airyscan and thus not specified in the following description. FISH dot identification relied on 2D local maxima identification and alignment. Initially for each frame, 2D maxima above a low threshold value were identified. Each 2D local maximum regarded its projection on the neighboring z-slices for alignment: those that fall within 0.08 um were assigned to the same FISH dot. The pixels with maximal intensities (pseudo-3D-maxima) for identified FISH dots were extracted for further analysis.

Signal-to-noise ratio (SNR) and contrast were generated adaptively for each individual FISH dot. To this end, pixel values (local background) were taken from a square centered around the pseudo-3D-maxima, excluding all circular regions covering the PSF (point spread function) for 2D maxima on the same plane. Contrast is defined as the ratio of the maximal intensity and the mean of its local background values; SNR, as traditionally defined, equals to maximal intensity divided by the standard deviation of local background values.

For color decoding in samples with Hulu-probe for multiple genes, the presence of fluorophore on each channel was initially separately determined. Dual or triple color coding was assigned when FISH dots from different channels co-localized within 0.08 um. Single color assignment required thresholding with a higher intensity, given there were three copies of fluorophores in the single-color Hulu-probe. Nuclei were manually segmented on the maximum intensity projected image in ImageJ. Without the assistance of membrane immunostaining, each identified FISH dot was assigned to its closest nuclei.

References

1. Gall, J. G. & Pardue, M. L. Formation and Detection of Rna-Dna Hybrid Molecules in Cytological Preparations. Proc. Natl. Acad. Sci. 63, 378-383 (1969).

2. Femino, A. M., Fay, F. S., Fogarty, K. & Singer, R. H. Visualization of Single RNA Transcripts in Situ. Science 280, 585-590 (1998).

3. Raj, A., van den Bogaard, P., Rifkin, S. A., van Oudenaarden, A. & Tyagi, S. Imaging individual mRNA molecules using multiple singly labeled probes. Nat Meth 5, 877-879 (2008).

4. Lubeck, E., Coskun, A. F., Zhiyentayev, T., Ahmad, M. & Cai, L. Single-cell in situ RNA profiling by sequential hybridization. Nat. Methods 11, 360-361 (2014).

5. Chen, K. H., Boettiger, A. N., Moffitt, J. R., Wang, S. & Zhuang, X. Spatially resolved, highly multiplexed RNA profiling in single cells. Science aaa6090 (2015). doi: 10.1126/science.aaa6090

6. Lubeck, E. & Cai, L. Single-cell systems biology by super-resolution imaging and combinatorial labeling. Nat. Methods 9, 743-748 (2012).

7. Levesque, M. J. & Raj, A. Single-chromosome transcriptional profiling reveals chromosomal gene expression regulation. Nat. Methods 10, 246-248 (2013).

8. Raj, A. & Tyagi, S. in Methods in Enzymology 472, 365-386 (Elsevier, 2010).

9. Lyubimova, A. et al. Single-molecule mRNA detection and counting in mammalian tissue. Nat. Protoc. 8, 1743-1758 (2013).

10. Tsanov, N. et al. smiFISH and FISH-quant—a flexible single RNA detection approach with super-resolution capability. Nucleic Acids Res. gkw784 (2016). doi:10.1093/nar/gkw784

11. Untergasser, A. et al. Primer3-new capabilities and interfaces. Nucleic Acids Res. 40, e115-e115 (2012).

12. Wright, E. S., Yilmaz, L. S., Corcoran, A. M., Ökten, H. E. & Noguera, D.R. Automated Design of Probes for rRNA-Targeted Fluorescence In Situ Hybridization Reveals the Advantages of Using Dual Probes for Accurate Identification. Appl. Environ. Microbiol. 80, 5124-5133 (2014).

13. Roy, R., Hohng, S. & Ha, T. A practical guide to single-molecule FRET. Nat. Methods 5, 507-516 (2008).

14. Zhuang, X. et al. Fluorescence quenching: A tool for single-molecule protein-folding study. Proc. Natl. Acad. Sci. 97, 14241-14244 (2000).

15. Zuker, M. Mfold web server for nucleic acid folding and hybridization prediction. Nucleic Acids Res. 31, 3406-3415 (2003).

16. Pau, G., Fuchs, F., Sklyar, O., Boutros, M. & Huber, W. EBImage-an R package for image processing with applications to cellular phenotypes. Bioinformatics 26, 979-981 (2010).

The invention claimed is:

1. A method for producing a labeled, or otherwise modified, oligonucleotide probe, the method comprising the steps of:

(a) providing a probe-sequence-oligonucleotide comprising (i) a probe sequence comprising a nucleotide sequence complementary to a target nucleic acid and (ii) a predetermined tag nucleotide sequence complementary to a first adaptor nucleotide sequence, (b) providing a label-carrier-oligonucleotide comprising at least one labeling moiety, or other functional moiety, wherein the label-carrier-oligonucleotide has a predetermined tag nucleotide sequence complementary to a second adaptor nucleotide sequence, (c) providing an adaptor-oligonucleotide, comprising in direct sequence and on a single strand, the first and the second adaptor nucleotide sequence;

(d) bringing into contact under hybridizing conditions the probe-sequence-oligonucleotide, the label-carrier-oligonucleotide and the adaptor-oligonucleotide, to form a complex, wherein, in the complex, a free/unblocked 3'-OH group is in close spatial proximity to a free/ unblocked 5' phosphate group, (e) reacting the complex to form a covalent bond between the 3'-OH group and the 5'-phosphate group using a ligase under ligating conditions, and (f) removing the adaptor-oligonucleotide to form the labeled, or otherwise modified, oligonucleotide probe.

2. The method for producing the labeled, or otherwise modified, oligonucleotide probe according to claim 1, wherein:

in the probe-sequence-oligonucleotide, the probe sequence is 5' of the predetermined tag nucleotide sequence, in the adaptor-oligonucleotide, the first and second adaptor nucleotide sequence are in 3' to 5' direction in direct sequence, the free/unblocked 3'-OH group is located on the probe-sequence-oligonucleotide and the free/unblocked 5'-phosphate group is located on the label-carrier-oligonucleotide, and in the complex in step (d), the free/unblocked 3'-OH group of the probe-sequence-oligonucleotide is in close spatial proximity to the free/unblocked 5'-phosphate group of the label-carrier-oligonucleotide.

3. The method for producing the labeled, or otherwise modified, oligonucleotide probe according to claim 1, wherein:

in the probe-sequence-oligonucleotide, the probe sequence is 3' of the predetermined tag nucleotide sequence, in the adaptor-oligonucleotide, the first and second adaptor nucleotide sequence are in 5' to 3' direction in direct sequence, the free/unblocked 3'-OH group is located on the label-carrier-oligonucleotide and the free/unblocked 5'-phosphate group is located on the probe-sequence-oligonucleotide, and in the complex in step (d), the free/unblocked 5'-phosphate group of the probe-sequence-oligonucleotide is in close spatial proximity to the free/unblocked 3'-OH group of the label-carrier-oligonucleotide.

4. The method for producing the labeled, or otherwise modified, oligonucleotide probe according to claim 1, wherein step (b) comprises providing a first, and a second, optionally a third or more, label-carrier-oligonucleotides, wherein the first label-carrier-oligonucleotide has a predetermined tag nucleotide sequence complementary to a second adaptor nucleotide sequence, the second label-carrier-oligonucleotide has a predetermined tag nucleotide sequence complementary to a third adaptor nucleotide sequence, optionally, the third or more label-carrier-oligonucleotide has a predetermined tag nucleotide sequence complementary to a fourth or more adaptor nucleotide sequence, and wherein in step (c) the adaptor-oligonucleotide comprises in direct sequence the first, the second, the third, optionally the fourth or more, adaptor nucleotide sequence.

5. The method according to claim 4, wherein each of the adaptor nucleotide sequences comprises distinct nucleotide sequences.

6. The method according to claim 4, wherein each of the label-carrier-oligonucleotides is differently labeled or otherwise modified.

7. The method according to claim 1, wherein the label-carrier-oligonucleotide comprises two or more labeling moieties.

8. The method according to claim 7, wherein the two or more, labeling moieties comprise at least two or more different labeling moieties, or other functional moieties.

9. The method according to claim 1, comprising purifying the labeled, or otherwise modified, oligonucleotide probe.

10. The method according to claim 1, wherein the probe-sequence-oligonucleotide has a length of between 20 to 300 nucleotides.

11. A method for generating a single molecule Fluorescent In-Situ Hybridization (smFISH) probe library, comprising producing at least two fluorescent labeled oligonucleotide probes according to the method of claim 1, wherein the labeling moiety is a fluorescent moiety, and wherein the at least two fluorescent oligonucleotide probes are capable of binding to one target nucleic acid.

12. The method according to claim 11, wherein the at least two fluorescent labeled oligonucleotide probes are at least 10 fluorescent labeled oligonucleotide probes, and wherein each of the fluorescent labeled oligonucleotide probes is capable of binding to the one target nucleic acid.

13. The method according to claim 1, wherein the labeled, or otherwise modified, oligonucleotide probe is single-stranded.

* * * * *